United States Patent [19]

Kobayashi

[11] Patent Number: 5,546,142
[45] Date of Patent: Aug. 13, 1996

[54] METHOD AND APPARATUS OF OPTOMETRY

[75] Inventor: Katsuhiko Kobayashi, Tokyo, Japan

[73] Assignee: Kabushiki Kaisha Topcon, Tokyo, Japan

[21] Appl. No.: 317,592

[22] Filed: Oct. 3, 1994

[30] Foreign Application Priority Data

Oct. 4, 1993 [JP] Japan .................... 5-269505

[51] Int. Cl.$^6$ ........................... A61B 3/02
[52] U.S. Cl. .................. 351/237; 351/239; 351/246
[58] Field of Search ................... 351/211, 221, 351/247, 237, 239, 243, 246

[56] References Cited

U.S. PATENT DOCUMENTS 4,740,071  4/1988  Kobayashi .................. 351/211

Primary Examiner—William L. Sikes
Assistant Examiner—Hung Xung Dang
Attorney, Agent, or Firm—Ronald P. Kananen

[57] ABSTRACT

A method and apparatus of optometry, which lets a subject observe an optometrical target through a correcting optical system having a variable refractive power, are designed to measure the optical characteristics of the subject with a measuring means, and display on a display means a target image as the case of the observation of a prescribed target by the subject, based on the measured optical characteristics of the subject.

8 Claims, 7 Drawing Sheets

$D_1 : S_1, C_1, A_1$
$D_2 : S_2, C_2, A_2$
$D_0 : S_0, C_0, A_0$

METHOD AND APPARATUS OF OPTOMETRY

BACKGROUND OF THE INVENTION

The present invention relates to a method and apparatus of optometry.

In the conventional method and apparatus of optometry, a split target having a special shape (e.g., slit shape) is projected on to the fundus of a subject and the refractive power of the subjects eye is measured based on the split value. This method is called "objective optometry". Alternatively, a person being tested under test) is requested to observe an optometrical target such as a landolt's ring through a correcting optical system, which is adjusted until the person is able to clearly see the target. The refractive power is indicated by the amount of adjustment. This method is known as "subjective optometry".

The method and apparatus of objective optometry is advantageous in that a person under test does not need to make a response, while the apparatus of subjective optometry is superior in connection with determining optimal correcting power for the subject. In this connection, a method adopted recently involves a) using an objective optometry apparatus to measure the approximate correcting power, thus obviating the awkwardness involved with having a person respond during testing the resulting inaccuracy of measurement; and thereafter b) using a separate or built-in subjective optometry apparatus to determine the final correcting power based on measurements using objective optometry.

There has been proposed a subjective optometry apparatus in which a target image on the fundus of a subject is formed on an imaging device and the target image signal is multiplied by a signal response function after the retina so that the inspector can view the same target image as that the person under test is observing. Refer to Japanese Patent Publication No. 4-17047.

For more accurate measurement by eliminating an erroneous response made by a person under test, it is desirable for the above-mentioned subjective optometry apparatus to enable the inspector to view the state of observation of the person, however, this is not feasible with the conventional apparatus.

Even if it is intended to let a person under test observe a target for subjective optometry and to view the target image formed on the fundus of the subject by means of a general imaging device, it is difficult to get a clear target image due to a low reflectivity of the fundus and a low sensitivity of the imaging device.

SUMMARY OF THE INVENTION

An object of the present invention is to provide a method and apparatus of optometry which enable the accurate observation of the optometrical target image on the fundus of a subject.

According to one preferred form of this invention, a method of optometry, which lets a subject observe an optometrical target through a correcting optical system having a variable refractive power, measures the optical characteristics of the subject and displays on a display means a target image as the case of the observation of the target by the subject based on the measured optical characteristics of the subject.

Preferably, the optometrical target is rendered as an image processing based on the convolution integral with the point spread attributable to the optical characteristics of the subject or the point spread determined from the signal produced by the measurement of the state of refractivity of the subject.

According to another form of this invention, an apparatus of optometry, which lets a subject observe an optometrical target through a correcting optical system having a variable refractive power, comprises means of measuring the optical characteristics of the subject and means of displaying a target image as the case of the observation of a prescribed target by the subject based on the measured optical characteristics of the subject.

Preferably, the measuring means includes a projection device for projecting a point pattern into the subject and a detection device for detecting the intensity distribution of the pattern image on the fundus of the subject, and the display means forms a target image or selects one of target images prepared in advance as the case of the observation of a prescribed target by the subject based on the spread data for the intensity distribution of the pattern image and target data for the target, and displays the target image.

The measuring means includes a projection device for projecting a slit-shaped or step-shaped pattern into the subject and a detection device for obtaining the point spread based on the intensity distribution in at least two directions of the pattern image on the fundus of the subject, and the display means forms a target image or selects one of target images prepared in advance as the case of the observation of a prescribed target by the subject based on the spread data for the intensity distribution and target data for the target, and displays the target image.

The measuring means includes a refractive power measuring device for measuring the refractive power of the subject, and the display means forms a target image or selects one of target images prepared in advance as the case of the observation of a prescribed target by the subject based on the refraction data of the subject provided by the refractive power measuring device and the data for the target, and displays the target image.

Alternatively, the measuring means includes a refractive power measuring device for measuring the refractive power of the subject, and the display means displays a target image similar to that in the case of the observation of a prescribed target by the subject based on the refraction data of the subject provided by the refractive power measuring device.

According to the present invention, the subjective optometry apparatus simulates a target image of the optometrical target on the fundus of a subject and displays it on the display means, and consequently the inspector who views target image can implement the accurate optometry by eliminating an erroneous response by of the person under test.

DESCRIPTION OF THE PREFERRED EMBODIMENTS

Figure 1:
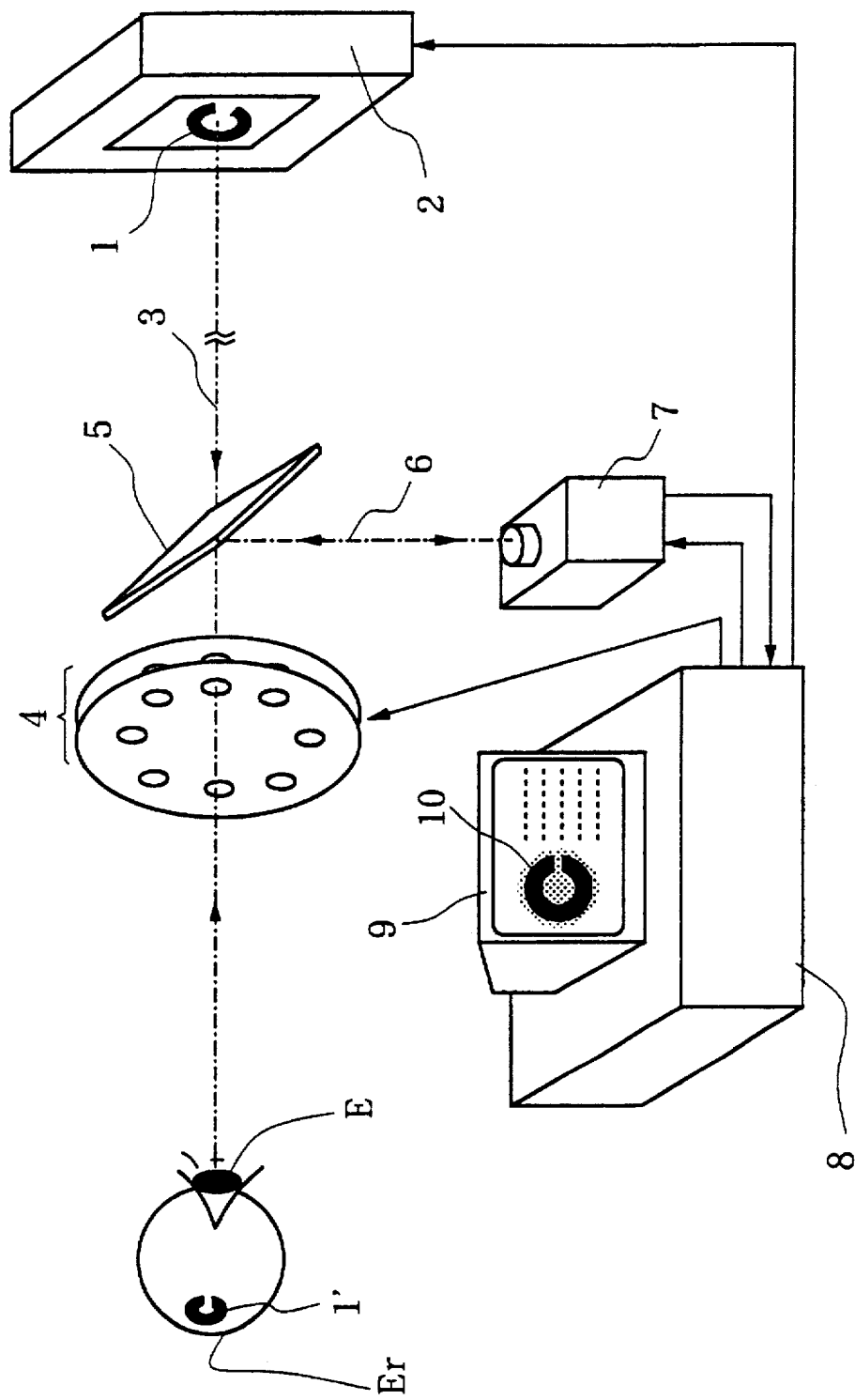
FIG. 1 is an explanatory diagram showing an example of the subjective optometry apparatus according to the present invention.

A subjective optometry apparatus shown in FIG. 1 includes a measuring means 7 for measuring a point spread attributable to the optical characteristics of a subject E, an image processing means (e.g., a computer 8) for implementing a convolution integral for the point spread, a target presenting device 2 which is operated by the inspector through the computer 8 to present a prescribed optometrical target 1, and a correcting optical system 4 which is located on the observation optical axis 3 and operated by the inspector through the computer 8 to correct the refractive power of the subject E. The subject E observes the optometrical target 1 through the correcting optical system 4, and an image 1' of the optometrical target 1 is formed on the fundus Er of the subject E.

A half-mirror 5 is disposed obliquely between the target presenting device 2 and correcting optical system 4 on the observation optical axis 3. The measuring means 7 for measuring the point spread attributable to the optical characteristics of the subject E is located on the reflection optical axis 6 of the half-mirror 5.

The measuring means 7 includes a projection device, e.g., a light source surface of an infrared point source (not shown), for projecting a point pattern into the subject E, and a detection device, e.g., a light sensitive surface of a light receiving device (not shown), for detecting the intensity distribution of the pattern image on the fundus of the subject E.

The optometrical target 1 and the infrared point source surface in the measuring means 7 are located such that they are conjugate with respect to the correcting optical system 4 and optical system of the subject E (eg. cornea etc.). The fundus Er and the light sensitive surface of the light receiving device (not shown) are located such that they are conjugate with reference to the correcting optical system 4 and optical system of the subject E.

Figure 3:
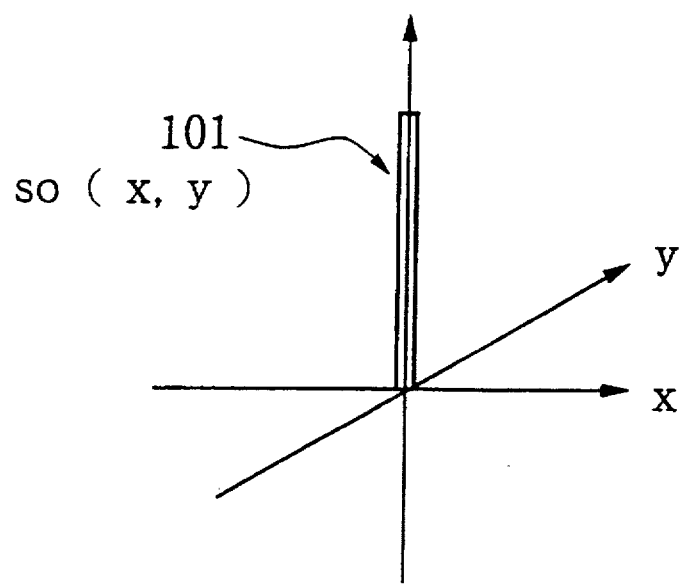
FIG. 3 is a graph showing the infrared point light source having a specific intensity distribution.
Figure 4:
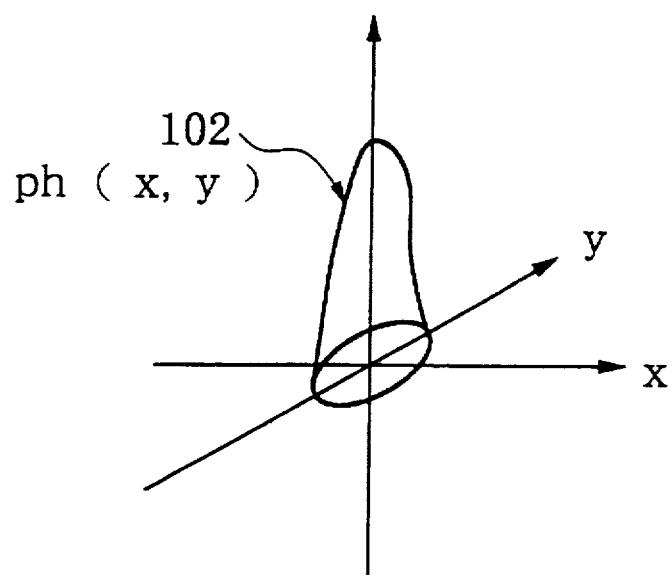
FIG. 4 is a graph showing the point image having a specific modulated intensity distribution.

The measuring means 7 projects an infrared point light source having an intensity distribution SO(x,y) as shown by 101 in FIG. 3 on to the fundus Er of the subject E through the correcting optical system 4 and optical system of the subject E. The infrared point light is modulated by the correcting optical system 4 and optical system of the subject E to form a point image 102 having a specific intensity distribution as shown in FIG. 4. The point image 102 goes back to the measuring means 7 through the optical system of the subject E, correcting optical system 4 and half-mirror 5, and it is focused on the light sensitive surface of the light receiving device (not shown). The focused image is modified and expressed as a point spread function ph(x,y) by the computer 8.

The computer 8 further implements the convolution integral for the image signal O(x,y), which represents the optometrical target 1, and the point spread function ph(x,y), and the image 1' of the optometrical target 1 formed on the fundus Er of the subject E is simulated based on the following formula.

$$i(x,y) = O(x,y)*ph(x,y) \qquad (1)$$
$$= \int \int_{-\infty}^{+\infty} O(x',y')Ph(x-x',y-y')dx'dy'$$

The simulated image 10 for the image 1' is displayed on a display means, e.g., a monitor screen, 9 shown in FIG. 1.

The display means, i.e., the monitor screen 9, forms a target image or selects one of target images prepared in advance as in the case of the observation of a prescribed target by the subject E based on the spread data for the intensity distribution of the pattern image and target data for the target, and displays the target image 10 of visibility.

For example, in the case wherein the measuring means 7 measures the line spread attributable to the optical characteristics of the subject E, the point spread is calculated by the image processing means (computer 8 in the example shown) based on the line spread in at least three directions centered by the optical axis 3 provided by the measuring means 7.

This feature will be explained with reference to FIG. 5 through FIG. 10.

Figure 5:
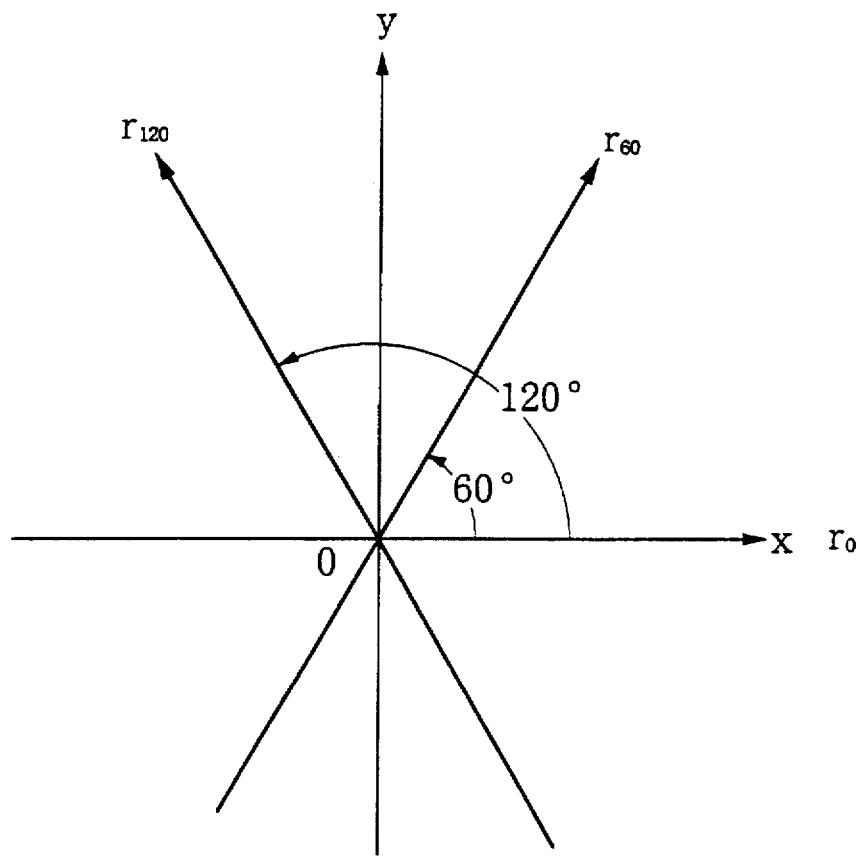
FIG. 5 is a graph showing the relationship among the $r_0$ axis, $r_{60}$ axis and $r_{120}$ axis.

As shown in FIG. 5, the $r_{60}$ axis and $r_{120}$ axis have angles of 60 and 120 degrees with respect to the x-axis ($r_0$ axis).

Figure 6:
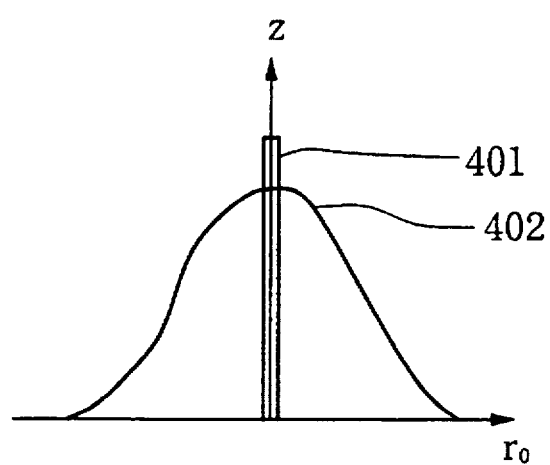
FIG. 6 is a graph showing the infrared line-shaped light source having an intensity distribution only in the $r_0$ axis direction.

The measuring means 7 projects an infrared line-shaped light source 401 having an intensity distribution only in the $r_0$ axis direction as shown in FIG. 6 on to the fundus Er of the subject E through the half-mirror 5, correcting optical system 4 and optical system of the subject E. The light is modulated by the correcting optical system 4 and optical system of the subject E to produce a specific line image 402 having an intensity distribution only in the $r_0$ direction.

Figure 7:
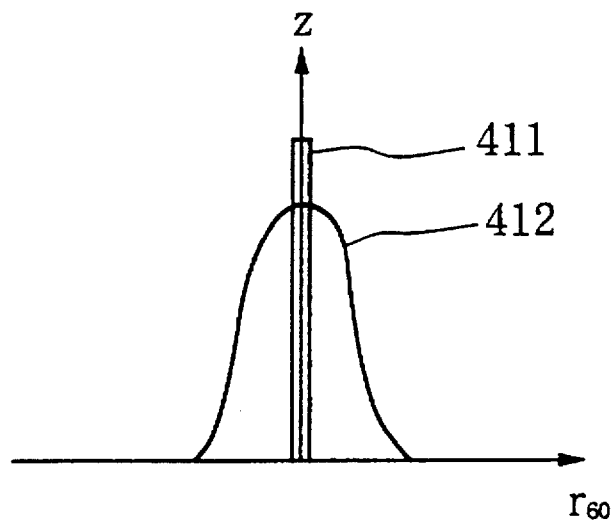
FIG. 7 is a graph showing the infrared line-shaped light source having an intensity distribution only in the $r_{60}$ axis direction.

The measuring means 7 projects an infrared line-shaped light source 411 having an intensity distribution only in the $r_{60}$ axis direction as shown in FIG. 7 on to the fundus Er of the subject E through the half-mirror 5, correcting optical system 4 and optical system of the subject E. The light is modulated by the correcting optical system 4 and optical system of the subject E to produce a specific line image 412 having an intensity distribution only in the $r_{60}$ direction.

Figure 8:
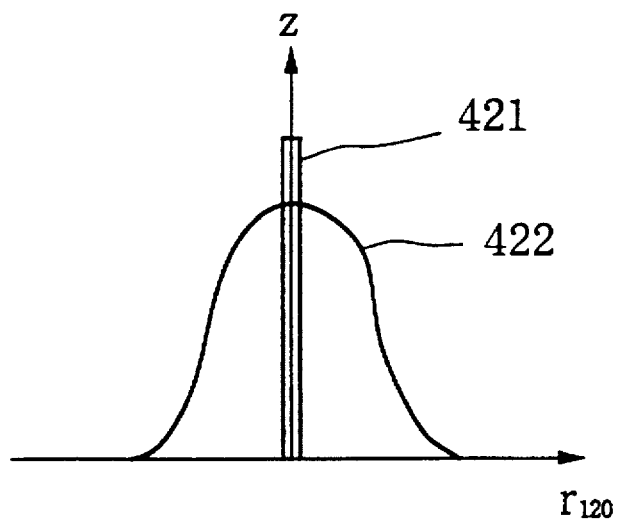
FIG. 8 is a graph showing the infrared line-shaped light source having an intensity distribution only in the $r_{120}$ axis direction.

The measuring means 7 projects an infrared line-shaped light source 421 having an intensity distribution only in the $r_{120}$ axis direction as shown in FIG. 8 onto the fundus Er of the subject E through the half-mirror 5, correcting optical system 4 and optical system of the subject E. The light is modulated by the correcting optical system 4 and optical system of the subject E to produce a specific line image 422 having an intensity distribution only in the $r_{120}$ direction.

These three line images 402, 412 and 422 are focused on the light sensitive surface of the light receiving device (not shown) in the measuring means 7 by way of the optical system of the subject E, correcting optical system 4 and half-mirror 5. The focused images are modified and expressed as point spread functions $ih(r_0)$, $ih(r_{60})$ and $ih(r_{120})$ by the computer 8.

The computer 8 calculates the major-axis length $A_2$, minor-axis length $B_2$ and the rotational angle $\theta$ of major axis with the x-axis of the ellipse on the plane at a certain intensity z from the three functions $ih(r_0)$, $ih(r_{60})$ and $ih(r_{120})$. Based on these values, the computer 8 calculates the point spread caused by the correcting optical system 4 and optical system of the subject E as an elliptic function on the plane at a certain intensity z as follows.

$$(x \cos \theta + y \sin \theta)^2/A^2 + (-x \sin \theta + y \cos \theta)^2/B^2 \qquad \ldots (2)$$

Figure 9:
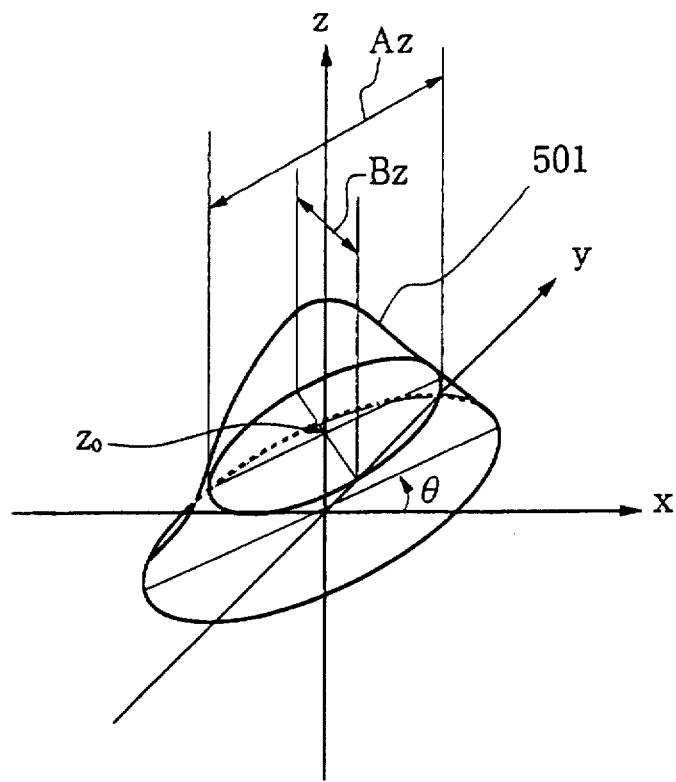
FIG. 9 is a graph showing an example of a computer calculated point spread function.

This elliptic function is calculated for several points on the z-axis of intensity, and through the interpolation process for the results, a point spread function $ph(x,y)$ attributable to the correcting optical system 4 and optical system of the subject E is finally obtained as shown by 501 in FIG. 9.

Figure 2:
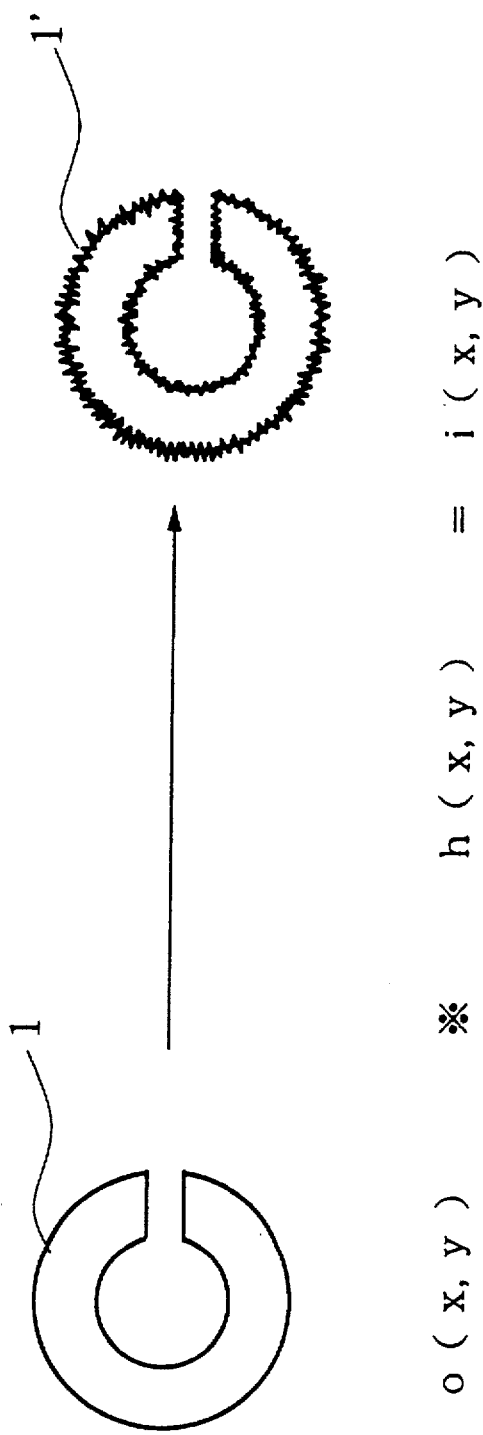
FIG. 2 is an explanatory diagram showing the relationship between the optometrical target and the simulated image.

The computer 8 implements the convolution integral for the image signal $O(x,y)$ of the optometrical target 1 and point spread function $ph(x,y)$ so that the image 1' of the optometrical target 1 formed on the fundus Er of the subject E is simulated as shown in FIG. 2. The simulated image 10 for the image 1' is displayed on the monitor screen 9 of the computer 8.

The symbol "*" used in FIG. 2 and formula (1) signifies convolution, and the symbol "x" used in the formulas (3), (4) and (5) signifies multiplication.

In another embodiment of this invention, the measuring means 7 includes a projection device (not shown) for projecting a slit-shaped or step-shaped pattern into the subject, and a detection device for detecting the point spread based on the intensity distribution in at least two directions of the pattern image on the fundus of the subject. The display means (computer) 9 forms a target image or selects one of target images prepared in advance as the case of the observation of the target by the subject based on the spread data for the intensity distribution and target data for the target, and displays the target image.

Figure 10:
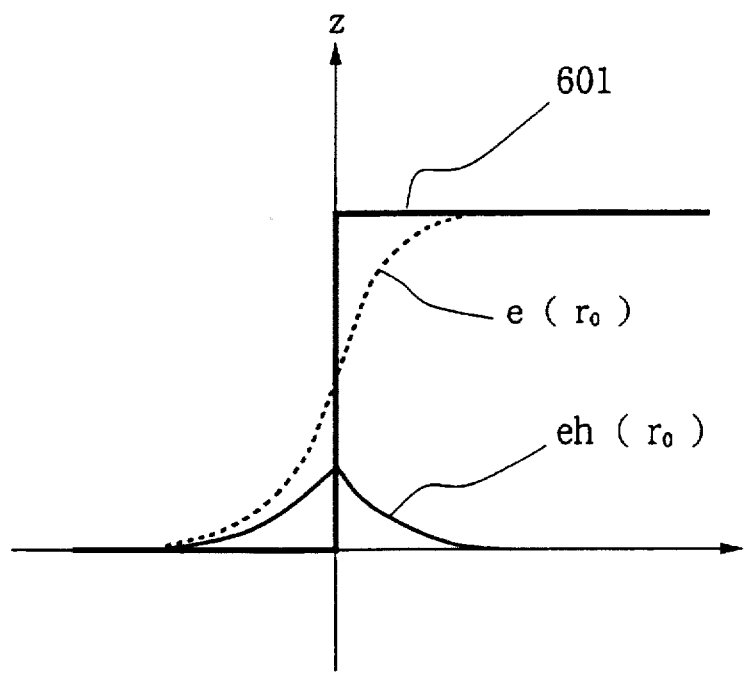
FIG. 10 is a graph showing the relationship between the step spread attributable to the optical characteristics of the subject and the point spread calculated from the former.

In the example of FIG. 10, the measuring means 7 measures the step spread attributable to the optical characteristics of the subject E. The image processing means (computer 8 in this example) calculates the point spread based on the step spread in at least three directions centered by the optical axis 3 provided by the measuring means 7.

This feature will be explained in more detail with reference to FIG. 10.

The measuring means 7 projects an infrared step-shaped light source 601 having an intensity distribution only in the $r_0$ axis direction as shown in FIG. 10 on to the fundus Er of a subject E through the half-mirror 5, correcting optical system 4 and optical system of the subject E. The light is modulated by the correcting optical system 4 and optical system of the subject E to produce a specific step image having an intensity distribution only in the $r_0$ direction.

The step image is focused on the light sensitive surface of the light receiving device (not shown) in the measuring means 7 by way of the optical system of the subject E, correcting optical system 4 and half-mirror 5, and modified by the computer 8 so that it is expressed as a step spread function $e(r_0)$. Subsequently, the computer 8 calculates $de(r_0/dr_0)$ to obtain the line spread function $eh(r_0)$ in the x-axis direction.

This operation is conducted for the three axes of $r_0$, $r_{60}$ and $r_{120}$ shown in FIG. 5, and $eh(r_0)$, $eh(r_{60})$ and $eh(r_{120})$ are obtained. Consequently, the measuring means 7 provides the point spread $ph(x,y)$ in the same manner as in the case of measuring the line spread attributable to the optical characteristics of the subject E.

The computer 8 implements the convolution integral for the image signal $O(x,y)$ of the optometrical target 1 and point spread function $ph(x,y)$ so that the image 1' of the optometrical target 1 formed on the fundus Er of the subject E is simulated as shown in FIG. 2. The simulated image 10 for the image 1' is displayed on the monitor screen 9 of the computer 8.

In still another embodiment of this invention, the measuring means 7 includes a refractive power measuring device (not shown) for measuring the refractive power of the subject. The display means (computer 8) forms a target image or selects one of target images prepared in advance as the case of the observation of a prescribed target by the subject based on the refraction data of the subject and target data for the target, and displays the target image.

For example, the measuring means 7 measures the state of refractivity of the subject. In this case, the image processing means (computer 8) determines the point spread function $ph(x,y)$ for the refractive power based on the refractive power of the subject E provided by the measuring means 7.

The computer 8 implements the convolution integral for the image signal $O(x,y)$ of the optometrical target 1 and point spread function $ph(x,y)$ so that the image 1' of the optometrical target 1 formed on the fundus Er of the subject E is simulated as shown in FIG. 2. The simulated image 10 for the image 1' is displayed on the monitor screen 9 of the computer 8.

Next, the method of measurement with the foregoing subjective optometry apparatus will be explained.

The inspector operates on the computer 8 to present an optometrical target 1 and have a person under test watch the target 1. The image 1' of the optometrical target 1 formed on the fundus Er of the subject E is simulated, and the result of simulation is displayed on the monitor screen 9. The inspector operates the correcting optical system 4 through the computer 8, while viewing the target image 10 displayed on the monitor screen 9, so that the image is brought in focus exactly. The refractive power of the subject E is evaluated from the correction value of the correcting optical system 4.

Figure 11:
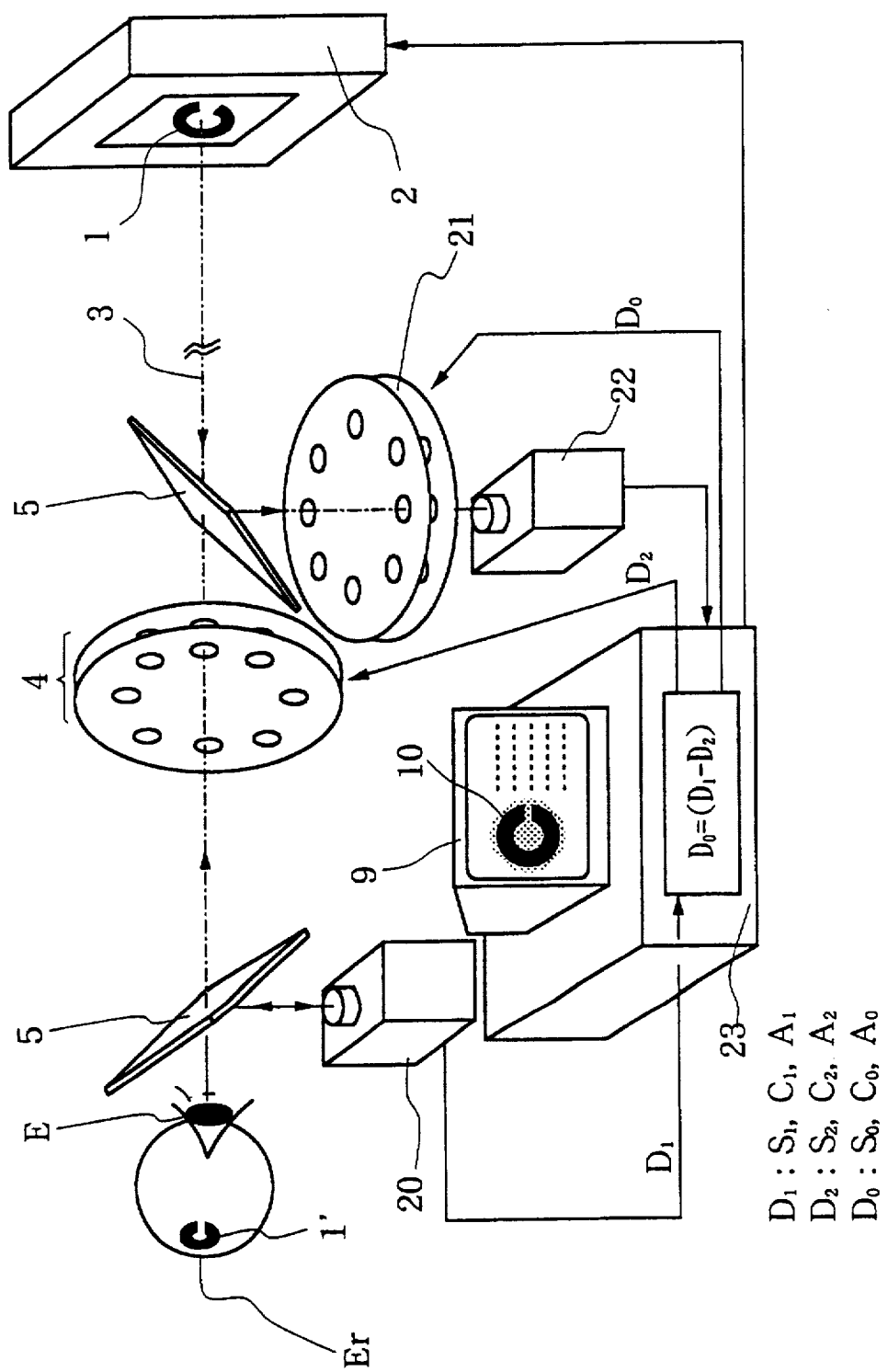
FIG. 11 is an explanatory diagram showing the subjective optometry apparatus according to another embodiment of this invention.

Next, still another embodiment of this invention (use of the correction value) will be explained with reference to FIG. 11.

A refractometer 20 is used to obtain the correction values $D_1$ of the subject E as refractive power data. The data consists of a sphere component $S_1$, a cylinder component $C_1$ and a cylinder axis angle $A_1$.

The refractometer 20 projects an annular light beam on to the fundus Er of the subject E, and evaluates the sphere component $S_1$ from the size of the formed image, the cylinder component $C_1$ from the shape of the ellipse, and the cylinder axis angle $A_1$ from the direction of major axis of the ellipse. The refractometer 20 used here is known in the art.

The correcting optical system 4 which is placed in front of the subject E is assumed to have correction values $D_2$ consisting of a sphere component $S_2$, cylinder component $C_2$ and cylinder axis angle $A_2$. The image processing means (computer 23) calculates residual correction values $D_0$ (consisting of sphere component $S_0$, cylinder component $C_0$ and cylinder axis angle $A_0$) based on $D_0 = -(D_1 - D_2)$, and operates on an adjusting optical system 21 for display to set the residual correction values $D_0$. A camera 22 used for display images the optometrical target 1 through the adjusting optical system 21 and delivers the produced image signal to the monitor screen 9. The monitor screen 9 forms an image of the optometrical target 1 based on the image signal provided by the camera 22.

The monitor screen 9 is adjusted in advance to display the image of the target 1 clearly (without blur) when the adjusting optical system 21 is given no refractive power.

Accordingly, when the correcting optical system 4 has a setup which uses the correction values provided by the refractometer 20, the adjusting optical system 21 is given no refractive power and it creates a clear image (without blur) of the target 1. The monitor screen 9 displays a clear (without blur) image 10 of the target 1.

In case the camera 22 used for display images the optometrical target 1 through the adjusting optical system 21 having a setup inclusive of some residual correction values $D_0$, the monitor screen 9 displays a blurred image 10 of the optometrical target 1 similar to that observed by the person under test.

The residual correction values $D_0=-(D_1-D_2)$ are calculated indivisually for the cylinder component $C_0$, sphere component $S_0$ and cylinder axis angle $A_0$ based on the following formulas (3), (4) and (5), respectively.

$$C_0=\{C_1^2+C_2^2-C_1\times C_2 \cos(A_2-A_1)\}^{1/2} \quad \ldots (3)$$

$$S_0=(S_1+S_2-C_0)/2 \quad \ldots (4)$$

$$A_0=(C_2\times\sin 2A_2-C_1\times\sin 2A_1)/(C_2\times\cos 2A_2-C_1\times\cos 2A_1) \quad \ldots (5)$$

I claim:

1. A method of optometry which lets a subject observe an optometrical target through a correcting optical system having a variable refractive power, said method comprising the steps of:

measuring optical characteristics of the subject; and simulating a target image as it would be observed by the subject based on the measured optical characteristics.

2. A method of optometry wherein a subject observes an optometrical target through a correcting optical system having a variable refractive power, comprising the steps of:

measuring the optical characteristics of the subject;

simulating a target image as it would be observed by the subject based on the measured optical characteristics of the subject; and image processing for implementing a convolution integral for the optometrical target and a point spread attributable to the optical characteristics of the subject.

3. An apparatus of optometry wherein a subject observes an optometrical target through a correcting optical system having a variable refractive power, said apparatus comprising:

measuring means for measuring optical characteristics of an eye of the subject; and simulation means for simulating a target image as it would be observed by the subject based on the optical characteristics measured by said measuring means.

4. An apparatus of optometry wherein a subject observes an optometrical target through a correcting optical system having a variable refractive power, said apparatus comprising:

measuring means for measuring optical characteristics of an eye of the subject; and display means for simulating a target image as it would be observed by the subject based on the optical characteristics measured by said measuring means;

wherein said measuring means includes a projection device for projecting a point pattern into the eye of the subject, and a detecting device for detecting an intensity distribution of a pattern image on a fundus of the eye of the subject, and wherein said display means forms the target image or selects one of pre-prepared target images based on spread data for the intensity distribution of the pattern image and target data for the target, and displays the simulated target image.

5. An apparatus of optometry wherein a subject observes an optometrical target through a correcting optical system having a variable refractive power, comprising:

measuring means for measuring optical characteristics of the subject;

display means for displaying a target image as a case of observation of a prescribed target by the subject based on the optical characteristics of the subject measured by said measuring means;

wherein said measuring means includes a projection device for projecting a slit-shaped or step-shaped pattern into the subject, and a detecting device for detecting a point spread based on the intensity distribution in at least two directions of the pattern image on the fundus of the subject and wherein said display means forms a target image or selects one of target images prepared in advance as the case of the observation of a prescribed target by the subject based on spread data for the intensity distribution and target data for the target, and displays the target image.

6. An apparatus of optometry wherein a subject observes an optometrical target through a correcting optical system having a variable refractive power, said apparatus comprising:

measuring means for measuring the optical characteristics of an eye of the subject; and display means for simulating a target image as it would be observed by the subject based on the optical characteristics measured by said measuring means; and wherein said measuring means includes a refractive power measuring device for measuring the refractive power of the eye of the subject, and wherein said display means forms the target image or selects one of pre-prepared target images based on refractivity data for the subject provided by said refractive power measuring device and data for a prescribed target, and displays the simulated target image.

7. An apparatus of optometry wherein a subject observes an optometrical target through a correcting optical system having a variable refractive power, said apparatus comprising:

measuring means for measuring the optical characteristics of an eye of the subject; and display means for simulating a target image as it would be observed by the subject based on the optical characteristics measured by said measuring means;

wherein said measuring means includes a refractive power measuring device for measuring the refractive power of the eye of the subject, and wherein said display means simulates the target image based on refractivity data for the subject provided by said refractive power measuring device.

8. A method of optometry wherein a subject observes an optometrical target through a correcting optical system having a variable refractive power, comprising the steps of:

measuring the optical characteristics of an eye of the subject;

simulating a target image as it would be observed by the subject based on the measured optical characteristics of the eye of the subject; and image processing for implementing the convolution integral for the optometrical target and a point spread determined from a signal produced by the measurement of a state of refractivity of the eye of the subject.

* * * * *